US006290656B1

(12) United States Patent
Boyle et al.

(10) Patent No.: US 6,290,656 B1
(45) Date of Patent: Sep. 18, 2001

(54) GUIDE WIRE WITH DAMPED FORCE VIBRATION MECHANISM

(75) Inventors: William J. Boyle, Fallbrook; Paul F. Muller, San Carlos, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,381

(22) Filed: Dec. 30, 1999

(51) Int. Cl.$^7$ .............................. A61B 5/00; A61M 25/00
(52) U.S. Cl. ............................................................ 600/585
(58) Field of Search ................................... 600/585, 434, 600/435, 159, 22, 191

(56) References Cited

U.S. PATENT DOCUMENTS

| | | | |
|---|---|---|---|
| 4,854,325 | * | 8/1989 | Stevens ................................ 600/585 |
| 5,243,997 | * | 9/1993 | Uflacker et al. ..................... 600/585 |
| 5,365,943 | | 11/1997 | Jansen . |
| 5,449,369 | * | 9/1995 | Imran .................................. 600/585 |
| 5,497,762 | | 3/1996 | Fugoso . |
| 5,549,119 | * | 8/1996 | Solar ................................... 600/585 |
| 5,666,968 | | 9/1997 | Imran et al. . |
| 5,908,395 | * | 6/1999 | Stalker et al. ....................... 600/585 |
| 5,925,059 | | 7/1999 | Palermo et al. . |

FOREIGN PATENT DOCUMENTS 663 541     12/1987  (CH) .
0 806 220   11/1997  (EP) .

* cited by examiner

Primary Examiner—Eric F. Winakur
Assistant Examiner—Brian Szmal
(74) Attorney, Agent, or Firm—Fulwider Patton Lee & Utecht, LLP (57) ABSTRACT

A guide wire having a damped force vibration mechanism which isolates vibrations or shockwaves which otherwise would be transmitted along the length of the guide wire to its distal end. The damped force vibration mechanism helps absorb some of the energy created during the exchange of a delivery catheter or an interventional device on the guide wire or any shock or force generated from an external source. The damped force vibration mechanism absorbs vibrations or shock which would otherwise act on medical devices attached near the distal end of a guide wire. The damped force vibration mechanism may consist of a reduced segment on the guide wire which can be made from a material such as superelastic or plastically deformable, biocompatible materials. The damped force vibration mechanism can have a relatively straight configuration or can have a wave-shaped form, or other shape which helps absorb vibratory motion.

54 Claims, 4 Drawing Sheets

FIG. 1

GUIDE WIRE WITH DAMPED FORCE VIBRATION MECHANISM

BACKGROUND OF THE INVENTION

The present invention relates generally to the field of guide wires for advancing intraluminal devices, such as stent delivery catheters, balloon dilatation catheters, atherectomy catheters and the like, within body lumens. The present invention is particularly directed to a guide wire having a medical device, such as an embolic filter, laser or ultrasonic cutting device, atherectomy device and the like, attached near its distal end for delivering the medical device into an area of treatment in a body lumen.

A variety of non-surgical interventional procedures have been developed over the years for opening stenosed or occluded blood vessels in a patient caused by the build up of plaque or other substances on the wall of the blood vessel. Such procedures usually involve the percutaneous introduction of an interventional device into the lumen of the artery, usually through a catheter. In typical PTCA procedures, a guiding catheter or sheath is percutaneously introduced into the cardiovascular system of a patient through the femoral artery and advanced through the vasculature until the distal end of the guiding catheter is in the ostium of the desired coronary artery. A guide wire is positioned within a lumen of a dilatation catheter and both devices are introduced through the guiding catheter to its distal end. The guide wire is first advanced out of the guiding catheter into the patient's coronary vasculature and is directed across the arterial lesion. The dilatation catheter is subsequently advanced over the previously advanced guide wire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter. Alternatively, a self-expanding stent could be expanded at the deployment site.

Another procedure for treating a stenosed region of an artery is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

The above non-surgical interventional procedures, when successful, avoid the necessity of major surgical operations. There is one common problem associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear offpieces of plaque which become embolic debris that can travel downstream and lodge somewhere in the patient's vascular system. Techniques have been developed to trap the emboli which include the placement of a filter or trap downstream from the treatment site to capture embolic debris before it reaches the smaller blood vessels downstream.

These above-mentioned devices can be placed within a body vessel usually in one of two ways. The device can be deployed into the area of treatment by advancing the device along a guide wire using over-the-wire techniques.

Alternatively, the device can be directly attached to the guide wire to allow the device to be placed in the patient's vasculature as the guide wire is moved into place by the physician. Once the guide wire is in proper position, the physician can operate the device to perform the desired procedure within the vasculature. The guide wire also can be used by the physician to deliver other interventional devices, such as a balloon angioplasty catheter or a stent delivery catheter, into the area of treatment.

Because of the environment that guide wires are used, and the purpose they serve, it is desirable to have several basic features for most, if not all, guide wires. The guide wire must be able to navigate and advance within the lumens of a patient, and come into contact with delicate tissue. For this reason, the guide wire usually requires a soft, flexible distal tip which can be manipulated without causing injury to the vessel walls. It also must be sufficiently maneuverable to reach the required destination, which requires stable torsional characteristics, and a rigid proximal shaft that can be pushed to advance the guide wire. This is particularly true when a medical device is attached near the distal end of the guide wire. Often, these characteristics are difficult to achieve, since one feature tends to negate the other. It is also desirable for the outer diameter of the guide wire to fit properly within the inside diameter of the lumen within which it is disposed.

Conventional guide wires for use in angioplasty, stent delivery, atherectomy and other vascular procedures generally comprise an elongated core member with one or more tapered section near the distal end and a flexible body member such as a helical coil disposed about distal portion of the core member. A shapable member, which may be the distal end of the core member or a separate shapable ribbon secured to the distal end of the core member enables the physician to shape or curve the tip as needed for maneuvering purposes. Torquing means are provided on the proximal end of the core member to rotate, and thereby steer, the guide wire while it is being advanced through the patient's vasculature. The tip of the guide wire should be highly flexible and a traumatic so as not to damage or perforate the vessel while the portion behind the tip should be increasingly stiff to better support the medical device attached to the guide wire.

Further details of guide wires, and devices associated therewith for various interventional procedures can be found in U.S. Pat. No. 4,748,986 (Morrison et al.); U.S. Pat. No. 4,538,622 (Samson et al.); U.S. Pat. No. 5,135,503

(Abrams); U.S. Pat. No. 5,341,818 (Abrams et al.); and U.S. Pat. No. 5,345,945 (Hodgson et al.) which are hereby incorporated by reference in their entirety.

There can be some problems associated when the medical device is directly attached to the guide wire. For example, a shockwave (vibratory motion) can be developed during the exchange of the delivery catheter or other interventional device on the guide wire which will travel along the length of the guide wire and possibly ajar the deployed medical device. A shockwave can possibly result in trauma to the wall of the blood vessel since the medical device will experience the shock and will transmit that force to the vessel wall in a scrapping action. These types of occurrences are undesirable since they can cause trauma to the vessel which is detrimental to the patient's health and/or could possibly cause the medical device to be displaced within the vessel.

What has been needed is a guide wire for use in the coronary and the peripheral vasculatures, particularly the carotid arteries, which is capable of acting as a "shock absorber" to absorb some of the energy which may be generated during the exchange of medical devices over the guide wire or by some external source. Such a guide wire would thus reduce the amount of vibratory motion which can travel over the length of the guide wire and prevent the vibration or shock from acting on the medical device attached to the guide wire core. As a result, the medical device should not move significantly or cause damage to the vessel wall since much of the energy transmitted along the length of the guide wire will be intercepted before reaching the medical device. The present invention disclosed herein satisfies these and other needs.

SUMMARY OF THE INVENTION

The present invention is directed to a guide wire having a damped force vibration mechanism which isolates vibrations or shockwaves which otherwise would be transmitted along the length of the guide wire to its distal end. The damped force vibration mechanism helps absorb some of the energy created during the exchange of a delivery catheter or an interventional device on the guide wire or any shock or force generated from an external source. The damped force vibration mechanism also would help absorb the energy caused during in-vivo contractions of the coronary anatomy system. The present invention is particularly useful in isolating vibrations or shock which would otherwise act on medical devices attached near the distal end of a guide wire. Such applications include, but are not limited to, a guide wire with an ultrasonic or laser cutting equipment attached to it, or an embolic protection device, such as a filter element or distal protection balloon attached to the distal end of the guide wire. Still other applications using other medical devices are possible.

The damped force vibration mechanism would be located along the guide wire proximal to the attached medical devices and would isolate the forces normally generated during device exchanges, along with any other forces or shock waves which may be transmitted along the guide wire when the proximal end of the guide wire is handled by the physician. As a result, the attached device will be spared from the shock which would otherwise act on them and, as a result, should spare the vessel wall from possible trauma.

A guide wire made in accordance with the present invention could also be utilized with any conventional PTCA or PTC dilatation catheter or stent delivery catheter since shock generated during the delivery of the catheter also would be dissipated by the damped force vibration mechanism associated with the present invention. As a result of using a guide wire with a damped force vibration mechanism, the distal end of the guide wire should not twist or "snap" as much within the vessel, which also will help prevent possible trauma to the body vessel.

In one embodiment, the damped force vibration mechanism would be located proximal to the medical device attached to the guide wire. The damp force vibration mechanism consists basically of a reduced segment on the guide wire which can be made from a material such as superelastic or plastically deformable polymer, ceramic or composite structures which are biocompatible. The damped force vibration mechanism also can be made from a single piece of relatively straight metal or alloy, such as nickel titanium or stainless steel, or a composite structure formed in a wave-shaped pattern, configured from a shape memory alloy. Other suitable shapes which dissipate energy could be used. The reduced segment of the guide wire would be covered with an elastic or elastomer tubing to match the outer diameter of the guide wire, thus creating a smooth and continuous outer surface. Alternatively, an elastomeric material could also be placed over this reduced diameter portion of the guide wire to create a smooth and contiguous outer surface.

In another embodiment, the damp force vibration mechanism includes a tubular member, such as a hypotube, which is attached to one end of the core wire of the guide wire. The opposite end of the core wire is capable of longitudinal movement within the hypotube. This moveable end of the core wire includes a shaft portion which moves within an opening located at the end of hypotube which matches the geometry of the cross-section of the shaft. The opening can be created by crimping the end of the hypotube to match the geometry of the shaft. Alternatively, a plate-like member having an opening with the same cross sectional geometry of the shaft could be affixed to the end of the hypotube to allow the shaft to move longitudinally within the hypotube. The opening at the end of the hypotube allows torque to be transmitted from the proximal end of the guide wire through the dampening mechanism to the distal end of the guide wire to allow a physician to steer the guide wire through the patient's vasculature. An end stop located on the shaft abuts against an elastic member, such as a biocompatible material or a spring, which is positioned within the hypotube and acts as shock absorber to reduce and dissipate vibratory motion . Another spring placed within the hypotube maintains the end stop biased against the elastic member and also help in absorbing some of the vibratory motion which may be transmitted along the core wire of the guide wire.

In still another embodiment, the damped force vibration mechanism is again disposed on the core wire of the guide wire. In this particular embodiment, the proximal core wire has a shaft with an end stop which is located within a hypotube that is affixed to the proximal core wire. The distal core wire also has a shaft with an end stop which is moveable longitudinally within the hypotube. Both shafts are at least partially opposed to each other in the hypotube. Both shafts of the proximal and distal cores create a recessed region between end stops in which an elastic member (a piece of highly elastic material is placed. Since the shafts do not directly contact each other, the elastic member creates an interface for absorbing vibratory motion transmitted along the proximal portion of the core wire which would otherwise be transmitted to the distal portion of the core wire. The particular configuration of shafts allow torque to be transmitted from the proximal end of the guide wire to the distal end to allow the physician to steer the guide wire through the patient's vasculature.

These and other advantages of the present invention will become more apparent from the following detailed description thereof when taken in conjunction with the following exemplary drawings.

DETAILED DESCRIPTION OF THE PREFERRED EMBODIMENTS

Figure 1:
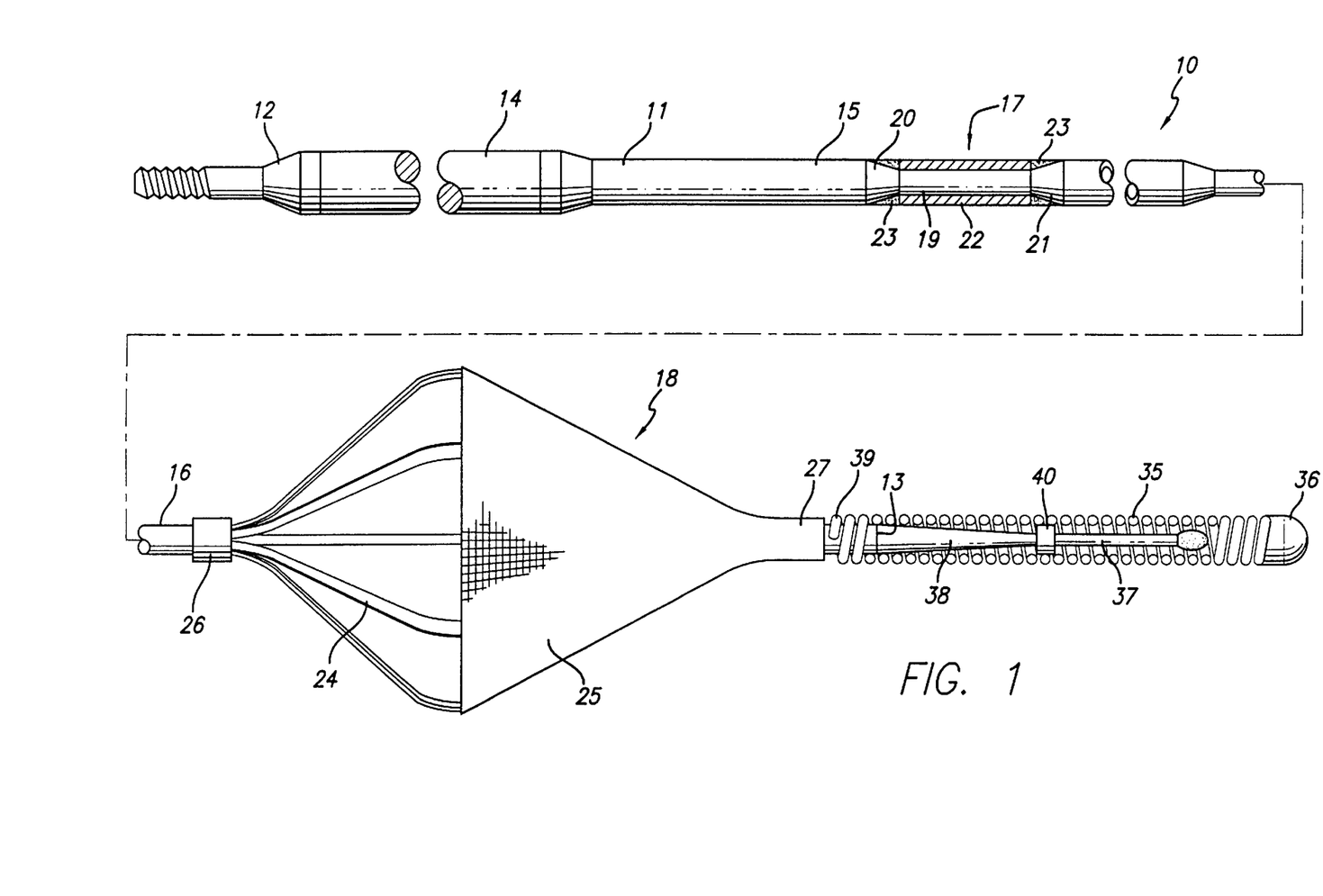
FIG. 1 is an elevational view of a guide wire which embodies features of the present invention.

FIG. 1 illustrates a guide wire 10 embodying features of the present invention which is adapted to be inserted into a patient's body lumen, such as an artery. The guide wire 10 comprises an elongated core member 11 having a proximal end 12 and a distal end 13. As can be seen in FIG. 1, the elongated core member 11 has a proximal portion 14 which has relatively high strength, an intermediate portion 15 and a distal portion 16. A damped force vibration mechanism 17 can be formed on the intermediate portion 15 of the guide wire 10. It should be appreciated, however, that the damped force vibration mechanism could also be placed on either of the other sections or portions of the guide wire. Preferably, the damped force vibration mechanism could be positioned approximately 5 to 50 cm from the distal tip of the guidewire. The actual damped force vibration mechanism position with respect to the tip of the guidewire would depend upon the anatomical region within the body being treated. Preferably, the damped force vibration mechanism would be positioned as far distal as possible, but still remain within a relatively straight segment of the guide catheter or sheath during an interventional procedure. Keeping the damped force vibration mechanism within a relatively straight portion of the guide or sheath would allow the device to absorb the maximum amount of energy along the axis of the guidewire system. A medical device, such as an embolic protection filter assembly 18, is located on the distal portion 16 of the guide wire 10. It also should be appreciated that although the invention is herein described in terms of an embolic protection filter assembly 18 attached to the guide wire 10, any number of medical devices, such as ultrasonic or laser cutting devices, flow rate sensors, atherectomy devices, and similar medical devices could be used in accordance with the present invention. In the particular embodiment shown in FIG. 1, this embolic protection filter assembly 18 is utilized to collect friable emboli which can enter the blood stream during the performance of an interventional procedure, such as a balloon angioplasty or a stenting procedure.

Figure 2:
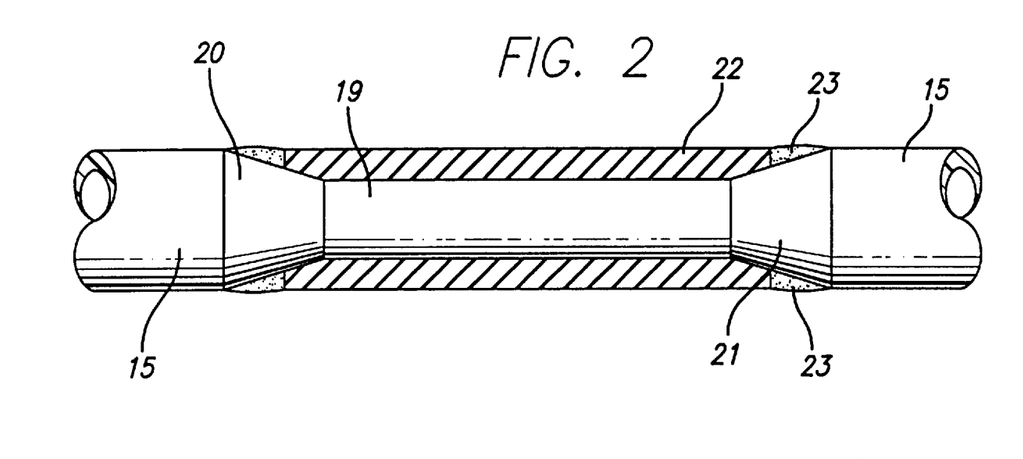
FIG. 2 is a side elevational view, partially in cross-section, of one embodiment of a damped force vibration mechanism made in accordance with the present invention.

Referring now to both FIGS. 1 and 2, the damped force vibration mechanism 17 is shown disposed on the intermediate portion 15 of the guide wire 10. This damped force vibration mechanism 17 consists basically of a reduced segment 19 formed on the guide wire 10 which is capable of acting as a "shock absorber" to absorb and prevent shock waves or vibrating forces from being transmitted to the embolic protection filter assembly 18. This segment 19 has a reduced diameter from adjacent portions of the guide wire and includes a first tapered portion 20 and a second tapered portion 21. This reduced segment 19 can be made from a super elastic or plastically deformable bio-compatible material, such as nickel titanium or stainless steel. Other suitable materials include biocompatible plastics and polymers. The reduced segment forming the damped force vibration mechanism does not compromise the guide wire's steering ability and the necessary torsional characteristics to maneuver to the required destination in the patient's vasculature. The rigid proximal shaft should be sufficiently strong to provide the pushability needed to advance the guide wire.

The reduced segment 19 can be covered by an elastic tubing 22 which matches the outer diameter of the intermediate portion 15 to create a smooth and continuous outer surface in this section of the guide wire 10. Due to the structure of the first and second tapered sections 20 and 21, a small amount of elastic filler material 23 may be required to be applied in the areas which would not be covered by the elastic tubing 22. Alternatively, the ends of the elastic tubing 22 could be cut with a taper to match the taper of the first and second tapered sections 20 and 21. This elastic tubing could be made from, for example, a piece of hypotube made from a nickel titanium alloy, or a piece of polymeric material, such as polyurethane.

The embolic protection filter assembly 18 includes a strut assembly 24 and a filter 25 attached to the strut assembly 24. The strut assembly 24 includes a proximal end 26 directly attached to the guide wire 10 at the distal portion of the guide wire. The distal end 27 of the strut assembly 24 moves freely along the length of the guide wire 10 to allow the assembly 24 to move between collapsed and expanded positions. In FIG. 1, the strut assembly 24 is shown in its expanded position as it would be deployed within an artery of a patient.

The damped force vibration mechanism 17 is located proximal to the embolic protection filter assembly 18 in order to isolate any vibration or shock waves which may be transmitted along the length of the guide wire 10 during usage. In this regard, the vibration mechanism 17 is typically located approximately 5 to 50 centimeters from the medical device (the embolic protection filter assembly 18) to achieve maximum vibration isolation and dampening during usage. Since the embolic protection filter assembly 18 may have a tendency to be displaced during device exchanges, the transmission of vibratory force along the length of the guide wire can cause the filter assembly 18 to possibly damage the wall of the vessel. The damping mechanism 17 would thus act as a "shock absorber" to absorb some or all of the energy transmitted along the guide wire and prevent that energy from acting on the filter assembly 18. As a result, possible trauma to the wall of the vessel would be averted.

Figure 3:
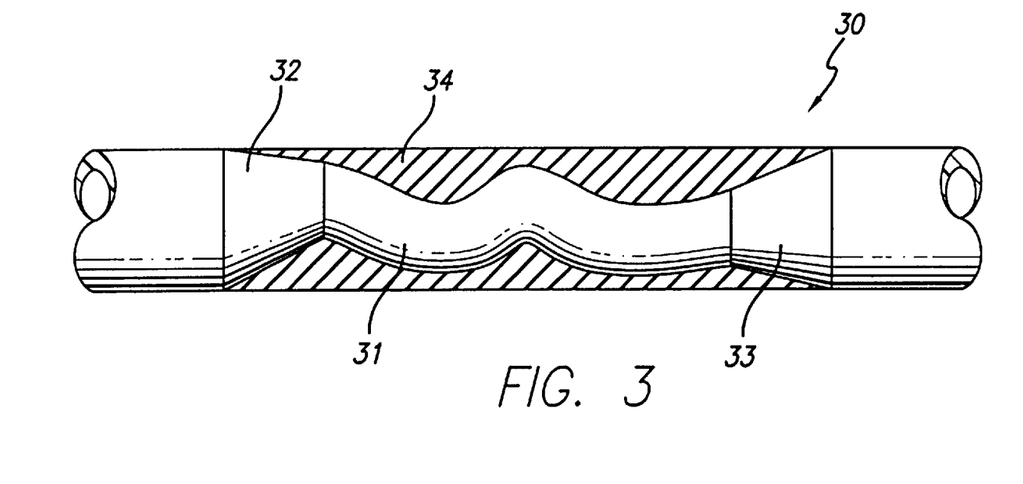
FIG. 3 is a side elevational view, partially in cross-section, of another embodiment of a damped force vibration mechanism made in accordance with the present invention.
Figure 4:
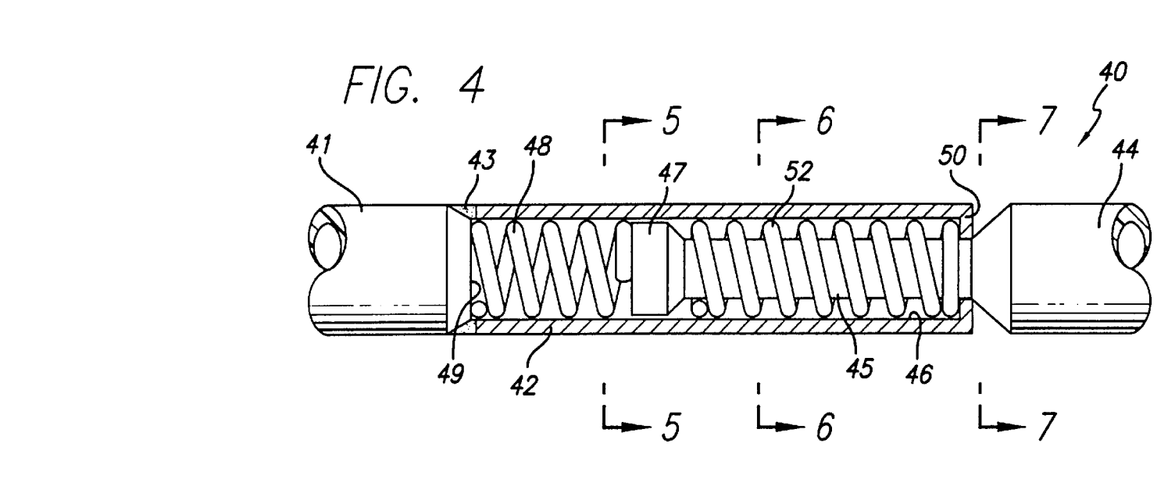
FIG. 4 is a side elevational view, partially in cross-section, of another embodiment of a damped force vibration mechanism made in accordance with the present invention.
Figure 5:
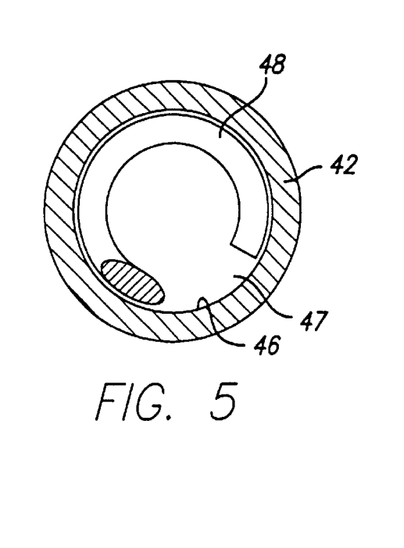
FIG. 5 is a cross sectional view of the damped forced vibration mechanism of FIG. 4 taken along lines 5—5.
Figures 6, 7:
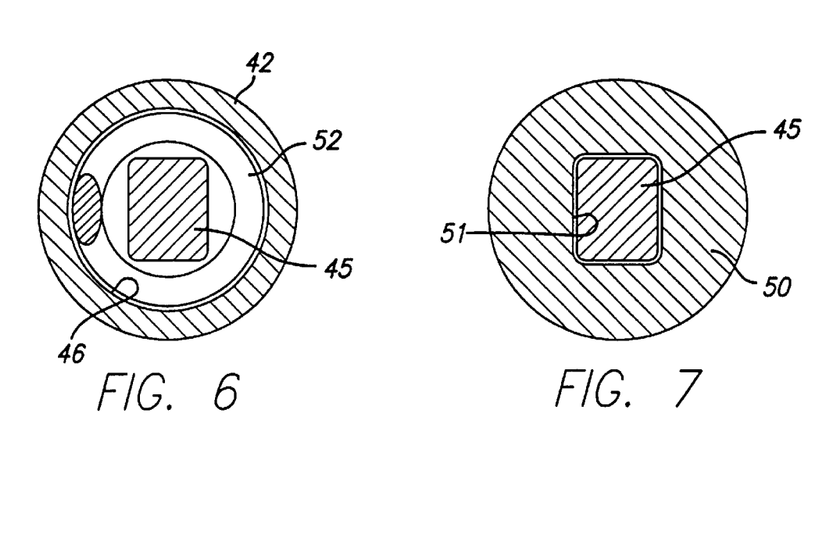
FIG. 6 is a cross sectional view of the embodiment of the damped force vibration mechanism of FIG. 4 taken along lines 6—6.
FIG. 7 is a cross sectional view of the embodiment of the damped force vibration mechanism of FIG. 4 taken along lines 7—7.

Referring now to FIG. 3, an alternative embodiment of a damped force vibration mechanism 30 is shown and described herein. This particular damped force vibration mechanism 30 would be located proximal to the filter assembly 18 in order to absorb some or all of the energy generated during, for example, the exchange of a balloon angioplasty device along the proximal end of the guide wire. This particular embodiment of the damped force vibration mechanism 30 also includes a reduced segment 31 which has a wave form shape that helps in absorbing the energy transmitted along the length of the guide wire. Other shapes which assist in absorbing the energy (vibratory motion) could also be implemented without departing from the spirit and scope of the present invention.

A first tapered section 32 and a second tapered section 33 are located at the end of the reduced segment 31 to provide a transition region on the guide wire. An elastomeric material 34 can be utilized and placed over the reduced segment 31 in order to create a smooth and contiguous outer diameter in this particular region of the guide wire. Alternatively, an elastic tubing, such a segment of hypotube, could be placed over the reduced segment 31. As with the previous embodiment, this damped force vibration mechanism 30 should be placed approximately 5 to 40 centimeters proximal to the medical device attached to the guide wire. In one preferred embodiment, the reduced segment 31 can be made from a shape memory alloy or a composite stainless steel material. Additionally, nickel titanium, a laminate structure of NiTi and stainless steel could also be utilized to form the reduced segment of the damped force vibration mechanism. Any of the above-listed materials could be used to form the damped force vibration mechanism regardless of which particular shape is selected, whether it be a straight segment, a wave-shaped segment or some other shock-absorbing shape.

The distal portion 16 of the guide wire 10 includes a helical coil 35 which extends from the core member 11 and creates an a traumatic tip which helps prevent the guide wire from puncturing or otherwise traumatizing the walls of the patient's vasculature. This helical coil 35 could be made from radiopaque material such as platinum or platinum nickel alloys to facilitate the observation thereof while it is disposed within the patient's vasculature. A rounded plug 36 is located at the distal end of the helical coil 35 to create a smooth a traumatic element which helps prevent the guide wire from puncturing or traumatizing the vessel wall of the patient. A shaping ribbon 37 is attached to a tapered section 38 of the distal portion 16 of the guide wire 10 to allow the physician to bend the tip of the guide wire, if necessary for steering purposes. The helical coil 35 is secured through the core member 11 at a proximal location 39 and to an intermediate location by solder or a suitable bonding method. The shaping ribbon 37 also can be soldered to the core member 11 or can be attached using suitable alternatives such as brazing, adhesives and the like. The guide wire 10 may be coated, at least in part, with a lubricious coating, such as a fluoropolymer, e.g., Teflon® available from DuPont, or Microglide® coating used by the present assignee, Advanced Cardiovascular Systems, Inc. on many of its commercial available guide wires. Hydrophillic coatings may also be used.

Referring now to FIGS. 4–7, an alternative embodiment of the damped force vibration mechanism 40 is shown and described herein. This particular damped force vibration mechanism 40 would also be located proximal to the filter assembly 18 in order to absorb some or all of the energy (vibratory motion) generated during, for example, the exchange of a balloon angioplasty device along the proximal end of the guide wire. This particular embodiment of the damped force vibration mechanism 40 includes a proximally located core wire 41 which has a tubular segment of material 42, made from a material such as a segment of hypotube, affixed thereto. The tubular segment 42 can be bonded to the proximal core wire 41 using suitable techniques such as a solder joint 43. Alternatively, other suitable methods such as brazing or adhesives can be used to connect these two elements together. A distal core wire 44 includes a shaft member 45 which extends within the lumen 46 of the tubular segment 42 and moves longitudinally within that lumen 46. An end stop 47 attached to the shaft member 45 has an outer diameter approximately the same as the inner diameter of the tubular segment 42 to allow the shaft to slide smoothly within the lumen 46. An elastic member 48, such as a spring or a piece of elastomeric material, can be positioned between the end stop 47 and the back stop 49 of the proximal core wire 41. The elastic member 48 provides an interface between the proximal core wire 41 and distal core wire 44 to dissipate and absorb vibratory motion which would otherwise be transmitted over the proximal core wire 41 to the distal core wire 44. Again, while a spring is used as the elastic member 48 in this particular embodiment, the elastic member 48 can be any particular material which helps to absorb vibration and prevent the vibration from being transmitted further to the distal core wire 44.

The end of the tubular segment 42 is attached to a plate-like member 50 which has an opening 51 that corresponds to the geometric cross sectional shape of the shaft 45. The plate like member 50 can be soldered, brazed, or adhesively affixed to the distal end of the tubular segment 42. Alternatively, a crimp placed at the end of the tubular segment 42 which corresponds to the cross sectional area of the shaft 45 would also allow the shaft 45 to move longitudinally within the tubular segment 42. A biasing element 52, such as a spring, is placed within the lumen 46 of the tubular segment 42 to help maintain end stop 47 biased against the elastic member 48. Alternative means for biasing the end stop 47 against the elastic member 48 could also be utilized in accordance with the present invention.

In use, the shaft 45 moves longitudinally within the lumen 46 of the tubular segment 42 while the elastic member 48 helps provide a shock absorbing element for preventing at least a portion of the transmission of vibratory motion from the proximal core wire 41 to the distal core wire 44. The biasing element 52 also helps some what in absorbing shock which may be transmitted along the proximal core wire 41 as well. The opening 51 in the plate-like member 50 allows the transmission of torque from the proximal core 41 to the distal core 44 to enable a physician to properly steer and manipulate the distal end of the guide wire into the patient's vasculature. It should be appreciated that although a rectangularly-shaped shaft 45 is shown in this particular embodiment, any number of different cross sectional shapes could also be used to create the shaft 45 without departing from spirit and scope of the present invention.

Figure 8:
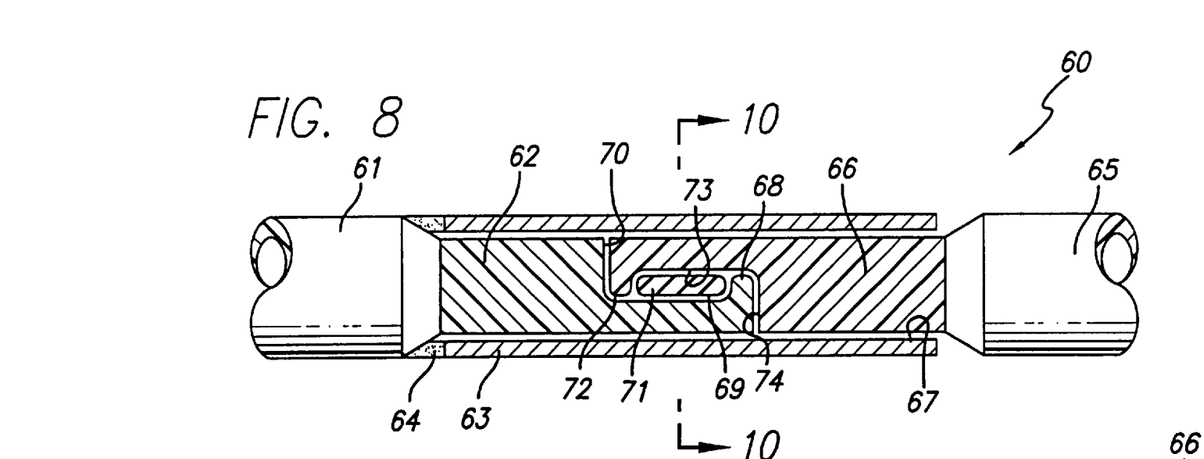
FIG. 8 is a side elevational view, partially in cross section of another embodiment of a damped force vibration mechanism made in accordance with the present invention.
Figure 9:
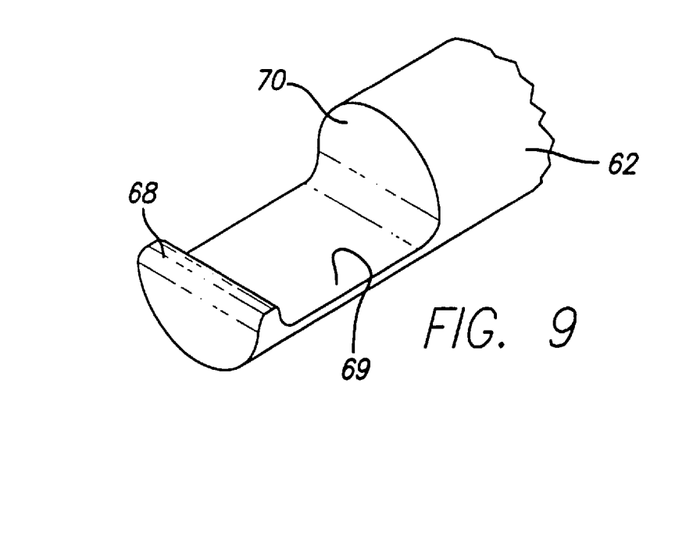
FIG. 9 is a perspective view of a portion of the semi circular shaft of the proximal core wire which forms part of the damped force vibration mechanism of FIG. 8.
Figure 10:
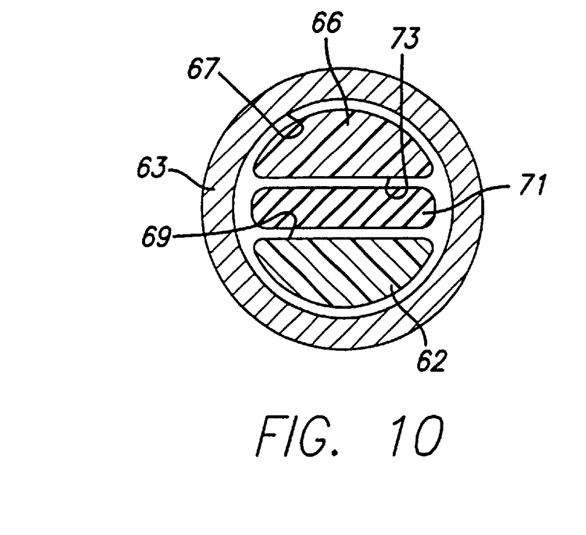
FIG. 10 is a cross sectional view of the embodiment of the damped force vibration mechanism of FIG. 8 taken along lines 10—10.

Referring now to FIGS. 8–10, another embodiment of a damped force vibration mechanism 60 is shown and described herein. This particular damped force vibration mechanism 60, like the previously described damped force vibration mechanisms, would be located proximal to the filter assembly 18 in order to absorbed some or all of the energy transmitted along the proximal end of the guide wire. This particular embodiment of the damped force vibration mechanism 60 includes a proximal core wire 61 which includes a shaft member 62 that is placed within a tubular segment 63, made from, for example, a length of hypotube, that is affixed to the proximal wire 61. Again, this tubular segment 63 can be affixed to the proximal core wire 61 using solder joint 64 or other suitable means for joining these two elements. The distal core wire 65 has a similar shaft member 66 located within the tubular segment 63. Each of the shaft members 62 and 66 are substantially the same except they are oriented directly opposite each other in the lumen 67 of the tubular segment 63. The shaft member 62 includes an end stop 68 and a recessed portion 69 which extends between end stop 68 and the proximal shoulder 70 formed on the shaft 62. This recessed portion 69 can be substantially flat area designed to receive an elastomeric member 71 which helps to dissipate at least some of the vibratory motion that would otherwise be transmitted to the distal core wire 65. The shaft member 66 of the distal core wire 65 also includes an end stop 72, a recessed portion 73 and a shoulder region 74. The area performed between the two end stops 68 and 72 and the two recessed portions 69 and 73 form a region where the elastomeric member 71 can be placed. In this manner, the proximal and distal core wires 61 and 65 never directly contact each other, with the elastomeric member 71 acting as an interface between these two elements to dissipate a vibratory motion which would otherwise be transmitted to the distal core wire 65. That elastomeric member 71 can be made from materials such as biocompatible polymers or rubbers. Alternative materials include low durometer polyurethanes. It should be appreciated that although this particular member 71 is shown as a somewhat rectangularly-shaped element in this embodiment, any number of different sizes and shapes could be utilized. Additionally, the size and shape of the recessed portions could also be varied without departing from the spirit and scope of the present invention.

In use, the shaft member 68 can move slightly within the tubular segment 63 relative to the other shaft member 62. Vibratory motion which may act upon the proximal core wire 61 would be transmitted to the shaft member 62 with the elastic member 71 acting as a buffer between shaft member 62 and shaft member 66 to absorb at least some of that vibratory motion and prevent that motion from being transmitted to the distal core wire 65. It should be appreciated that construction of the shaft members 62 and 66 permits torque to be transmitted to the distal end of the guide wire to allow the physician to properly steer and manipulate the guide wire within the patient's vasculature. While one particular configuration of the shaft member 62 and 66 are shown in FIGS. 8–10, it should be appreciated that other configurations could also be utilized without departing from the spirit and scope of the present invention.

The guide wire 10 can be made from about 43 inches (110 cm) to about 140 inches (355 cm) in overall length, but is preferred about 55 inches (140 cm) to about 122 inches (310 cm) in length. The core of the guide wire can be made from stainless steel and other conventional materials used to manufacture guide wires such as nickeltitanium. While the elongated core member 11 is shown having three discreet sections which have varying outer diameters, it should be appreciated to those skilled in the art that a number of different sections, each having different lengths and outer diameters, could be used in accordance with the present invention without departing from the spirit and scope of the present invention.

The core member 11 maybe formed of stainless steel, specifically 304V stainless steel, and NiTi alloys or combinations thereof as described in U.S. Pat. No. 5,341,818 (Abrams et al.) which has been incorporated by reference. Other materials which provide high strength to the elongated core also could be utilized without departing from the spirit and scope of the present invention. This hypotube used in accordance with the present invention can be made from a nickel titanium alloy, stainless steel or similar material. Additionally, proximal markers 40 and distal markers (not shown) can be applied to the guide wire to help visualize the location of the embolic protection filter assembly 18 within the patient's vasculature. Such markers can be made from a radiopaque material and can be soldered, brazed, bonded with a suitable adhesive, such as epoxy or cyanoacrylate, laser welded or mechanically crimped in place.

The outer diameter of the proximal portion 14 of the guide wire 10 is generally about 0.006 to 0.018 inches for coronary use. Wider diameter guide wires may be employed in peripheral arteries and other body lumens. The shaping ribbon and the distal portion of the guide wire can have cross-sectional diameter of about 0.001 to 0.003 inches.

While the above description of the invention is directed to the presently preferred embodiments, various modification improvements can be made to the invention while departing therefrom.

What is claimed:

1. A guide wire comprising:
   an elongated core member having distal and proximal ends; and
   a damped force vibration mechanism located on the elongated core member for at least partially absorbing a vibratory force which may travel along the length of the elongated core member and for preventing at least a portion of the vibratory force from traveling past the mechanism towards the distal end of the elongated core member.

2. The guide wire of claim 1, wherein the damped force vibration mechanism is made from a segment of material having a reduced diameter from the diameter of the elongated core member.

3. The guide wire of claim 2, wherein the segment of material forming the damped force vibration mechanism is different than the material making up the elongated core member.

4. The guide wire of claim 3, wherein the segment of material forming the damped force vibration mechanism is made from a superelastic alloy.

5. The guide wire of claim 2, wherein the segment of material forming the damped force vibration mechanism is made from a shape memory material.

6. The guide wire of claim 2, wherein the segment of material forming the damped force vibration mechanism is made from nickel-titanium alloy.

7. The guide wire of claim 2, wherein the segment of material forming the damped force vibration mechanism has a relatively straight shape parallel with the axis of the elongated core member.

8. The guide wire of claim 2, wherein the segment of material forming the damped force vibration mechanism has a wave shape construction.

9. The guide wire of claim 1, wherein the damped force vibration mechanism is placed near the proximal end of the elongated core member.

10. The guide wire of claim 1, wherein the elongated core member has a proximal portion and a distal portion and the damped force vibration mechanism is affixed between the proximal portion and distal portion.

11. The guide wire of claim 10, wherein the damped force vibration mechanism includes a tubular segment having an internal lumen and which is located on either the proximal or distal portion of the core wire and a shaft member located on either the proximal or distal portion of the guide wire, the shaft member being moveable longitudinally within the tubular segment with an elastic member disposed within the tubular segment and in contact with the shaft member to create an interface between the proximal and distal portion of the core member which at least partially absorbs vibratory force which may travel along the proximal portion of the elongated core member and prevents at least a portion of the vibratory force from traveling to the distal portion of the elongated core member.

12. The guide wire of claim 11, wherein the elastic member is a spring.

13. The guide wire of claim 11, wherein the elastic member is a piece of elastomeric material.

14. The guide wire of claim 11, further including a biasing element which biases the shaft member in contact with the elastic element.

15. The guide wire of claim 11, wherein the shaft member has a particular cross sectional area and the tubular segment has an opening with the same cross sectional area of the shaft member to allow the shaft member to pass therethrough.

16. The guide wire of claim 15, wherein a plate-like member is affixed to the distal end of the tubular segment and includes the opening which receives the shaft member.

17. The guide wire of claim 11, wherein the shaft member has an end stop which has substantially the same cross section shape as the inner lumen of the tubular segment.

18. The guide wire of claim 16, wherein the elastic member is placed in contact with the end stop.

19. The guide wire of claim 11, wherein the tubular segment is made from hypotube.

20. The guide wire of claim 10, wherein the damped force vibration mechanism includes a tubular segment having an internal lumen and which is located on either the proximal or distal portion of the core wire and a shaft member located on both the proximal or distal portion of the guide wire, the shaft members being housed within the tubular segment with an elastic member disposed between the shaft members to create an interface between the proximal and distal portion of the core member which at least partially absorbs vibratory force which may travel along the proximal portion of the elongated core member and prevents at least a portion of the vibratory force from traveling to the distal portion of the elongated core member.

21. The guide wire of claim 20, wherein each shaft member has a recessed area which forms a region in which the elastic member is placed.

22. The guide wire of claim 21, wherein each shaft member has an end stop which is in contact with the elastic member.

23. The guide wire of claim 20, wherein the elastic member is made from an elastomeric material.

24. The guide wire of claim 20, wherein each shaft member has a shape which conforms to the shape of the inner lumen of the tubular segment.

25. The guide wire of claim 11, wherein the tubular segment is made from hypotube.

26. A guide wire for delivering a medical device into a body vessel, comprising:

an elongated core member having distal and proximal ends;

a medical device attached to the core member; and a damped force vibration mechanism located on the elongated core member for at least partially absorbing a vibratory force which may travel along the length of the elongated core member to the medical device and for preventing at least a portion of the vibratory force from traveling past the mechanism to the medical device.

27. The guide wire of claim 26, wherein the damped force vibration mechanism is made from a segment of material having a reduced diameter from the diameter of the elongated core member.

28. The guide wire of claim 27, wherein the segment of material forming the damped force vibration mechanism is different than the material making up the elongated core member.

29. The guide wire of claim 28, wherein the segment of material forming the damped force vibration mechanism is made from a superelastic alloy.

30. The guide wire of claim 27, wherein the segment of material forming the damped force vibration mechanism is made from a shape memory material.

31. The guide wire of claim 27, wherein the segment of material forming the damped force vibration mechanism is made from nickel-titanium alloy.

32. The guide wire of claim 27, wherein the segment of material forming the damped force vibration mechanism has a relatively straight shape parallel with the axis of the elongated core member.

33. The guide wire of claim 27, wherein the segment of material forming the damped force vibration mechanism has a wave shape construction.

34. The guide wire of claim 27, wherein the segment of material forming the damped force vibration mechanism is made from a shape memory material.

35. The guide wire of claim 26, wherein the medical device is a filter for trapping emboli in the body vessel.

36. The guide wire of claim 26, wherein the medical device is a laser cutting device.

37. The guide wire of claim 26, wherein the medical device is an ultrasonic cutting device.

38. The guide wire of claim 26, wherein the clamped force vibration mechanism is placed about 5 to 50 centimeters proximal to the medical device.

39. The guide wire of claim 26, wherein the elongated core member has a proximal portion and a distal portion and the damped force vibration mechanism is affixed between the proximal portion and distal portion.

40. The guide wire of claim 39, wherein the damped force vibration mechanism includes a tubular segment having an internal lumen and which is located on either the proximal or distal portion of the core wire and a shaft member located on either the proximal or distal portion of the guide wire, the shaft member being moveable longitudinally within the tubular segment with an elastic member disposed within the tubular segment and in contact with the shaft member to create an interface between the proximal and distal portion of the core member which at least partially absorbs vibratory force which may travel along the proximal portion of the elongated core member and prevents at least a portion of the vibratory force from traveling to the distal portion of the elongated core member.

41. The guide wire of claim 40, wherein the elastic member is a spring.

42. The guide wire of claim 40, wherein the elastic member is a piece of elastomeric material.

43. The guide wire of claim 40, further including a biasing element which biases the shaft member in contact with the elastic element.

44. The guide wire of claim 40, wherein the shaft member has a particular cross sectional area and the tubular segment has an opening with the same cross sectional area of the shaft member to allow the shaft member to pass therethrough.

45. The guide wire of claim 44, wherein a plate-like member is affixed to the distal end of the tubular segment and includes the opening which receives the shaft member.

46. The guide wire of claim 40, wherein the shaft member has an end stop which has substantially the same cross section shape as the inner lumen of the tubular segment.

47. The guide wire of claim 46, wherein the elastic member is placed in contact with the end stop.

48. The guide wire of claim 40, wherein the tubular segment is made from hypotube.

49. The guide wire of claim 39, wherein the damped force vibration mechanism includes a tubular segment having an internal lumen and which is located on either the proximal or distal portion of the core wire and a shaft member located on both the proximal or distal portion of the guide wire, the shaft members being housed within the tubular segment with an elastic member disposed between the shaft members to create an interface between the proximal and distal portion of the core member which at least partially absorbs vibratory force which may travel along the proximal portion of the elongated core member and prevents at least a portion of the vibratory force from traveling to the distal portion of the elongated core member.

50. The guide wire of claim 49, wherein each shaft member has a recessed area which forms a region in which the elastic member is placed.

51. The guide wire of claim 50, wherein each shaft member has an end stop which is in contact with the elastic member.

52. The guide wire of claim 49, wherein the elastic member is made from an elastomeric material.

53. The guide wire of claim 49, wherein each shaft member has a shape which conforms to the shape of the inner lumen of the tubular segment.

54. The guide wire of claim 49, wherein the tubular segment is made from hypotube.

* * * * *